(12) United States Patent
Binder et al.

(10) Patent No.: US 12,297,166 B2
(45) Date of Patent: May 13, 2025

(54) PROCESSES FOR MAKING ETHYLENE GLYCOL AND/OR PROPYLENE GLYCOL FROM ALDOSE- AND/OR KETOSE-YIELDING CARBOHYDRATES WITH INTEGRATED TUNGSTEN CATALYST RECOVERY

(71) Applicant: T.EN Process Technology, Inc., Houston, TX (US)

(72) Inventors: Thomas P. Binder, Marion, IA (US); Louis A. Kapicak, Cross Lanes, WV (US)

(73) Assignee: T.EN Process Technology, Inc., Houston, TX (US)

( * ) Notice: Subject to any disclaimer, the term of this patent is extended or adjusted under 35 U.S.C. 154(b) by 0 days.

(21) Appl. No.: 18/616,840

(22) Filed: Mar. 26, 2024

(65) Prior Publication Data
US 2024/0262769 A1 Aug. 8, 2024

Related U.S. Application Data

(62) Division of application No. 18/099,072, filed on Jan. 19, 2023, now Pat. No. 11,958,794.
(Continued)

(51) Int. Cl.
*C07C 29/145* (2006.01)
*B01J 23/30* (2006.01)
(Continued)

(52) U.S. Cl.
CPC .............. *C07C 29/145* (2013.01); *B01J 23/30* (2013.01); *B01J 38/74* (2013.01); *C07C 29/76* (2013.01)

(58) Field of Classification Search
CPC ..... C07C 29/145; C07C 29/76; C07C 29/132; B01J 23/30; B01J 38/74
See application file for complete search history.

(56) References Cited

U.S. PATENT DOCUMENTS 4,279,869 A 7/1981 Coulson
10,138,184 B2 * 11/2018 Van Der Waal ...... C07C 31/202
(Continued)

OTHER PUBLICATIONS

International Search Report issued in PCT Application No. PCT/US2023/11150 on Jun. 21, 2023.

*Primary Examiner* — Jafar F Parsa
(74) *Attorney, Agent, or Firm* — Troutman Pepper Locke LLP (57) ABSTRACT

Integrated processes are disclosed for the catalytic conversion of carbohydrate to ethylene glycol and/or propylene glycol using a homogeneous, tungsten-containing retro-aldol catalyst. In these processes, the carbohydrate is subjected to retro-aldol conversion and hydrogenation to provide a reaction product containing ethylene glycol and/or propylene glycol, other reaction process including organic acids, itols and tungsten species. Ethylene glycol and propylene glycol are separated from the reaction product for purification, and at least a portion of the remaining fraction is subjected to ion exclusion chromatography to provide an eluant containing tungsten species and a subsequent eluant containing organic acids and a substantially reduced concentration of tungsten species. At least a portion of the eluant containing tungsten species can be recycled for reuse directly or with intervening unit operations to enhance the catalytic activity of the tungsten species. The organic-containing fraction can be subjected to one or more unit operations to provide salable products or subjected to selective hydrogenolysis to lower glycols.

2 Claims, 1 Drawing Sheet

Related U.S. Application Data (60) Provisional application No. 63/300,696, filed on Jan. 19, 2022.

(51) Int. Cl.
  *B01J 38/74* (2006.01)
  *C07C 29/76* (2006.01)

(56) References Cited

U.S. PATENT DOCUMENTS

| | | |
|---|---|---|
| 2017/0349513 A1 | 12/2017 | Schreck et al. |
| 2018/0362424 A1 | 12/2018 | Chewter et al. |
| 2021/0087128 A1 | 3/2021 | Schreck et al. |

* cited by examiner

PROCESSES FOR MAKING ETHYLENE GLYCOL AND/OR PROPYLENE GLYCOL FROM ALDOSE- AND/OR KETOSE-YIELDING CARBOHYDRATES WITH INTEGRATED TUNGSTEN CATALYST RECOVERY

CROSS-REFERENCE TO RELATED APPLICATION(S)

This application is a divisional of U.S. patent application Ser. No. 18/099,072, filed Jan. 19, 2023, which claims priority to U.S. Provisional Application No. 63/300,696, filed Jan. 19, 2022 and entitled "PROCESSES FOR MAKING ETHYLENE GLYCOL AND/OR PROPYLENE GLYCOL FROM ALDOSE- AND/OR KETOSE-YIELDING CARBOHYDRATES WITH INTEGRATED TUNGSTEN CATALYST RECOVERY," both of which are hereby incorporated by reference in its entirety under 35 U.S.C. § 119(e).

FIELD OF THE INVENTION

This invention pertains to processes for the catalytic production of ethylene glycol and/or propylene glycol from aldose- and/or ketose-yielding carbohydrates, particularly processes that have integrated tungsten catalyst recovery.

BACKGROUND

Ethylene glycol and propylene glycol are valuable commodity chemicals, and each has a broad range of uses. These chemicals are currently made from starting materials based upon fossil hydrocarbons (petrochemical routes).

Proposals have been made to manufacture ethylene glycol and propylene glycol from renewable resources such as carbohydrates, e.g., sugars. One such route has been practiced commercially and involves the fermentation of sugars to ethanol, catalytically dehydrogenating the ethanol to ethylene and the ethylene is then catalytically converted to ethylene oxide which can then be reacted with water to produce ethylene glycol. This route is not economically attractive as three conversion steps are required, and it suffers from conversion efficiency losses. For instance, the theoretical yield of ethanol is 0.51 grams per gram of sugar with, on a theoretical basis, one mole of carbon dioxide being generated per mole of ethanol.

Alternative processes to make ethylene glycol and propylene glycol from renewable resources are thus sought. These alternative processes include catalytic routes such as hydrogenolysis of sugar and a two-catalyst process using a retro-aldol catalyst ("retro-aldol route") to generate intermediates from sugar that can be hydrogenated over a hydrogenation catalyst to produce ethylene glycol and propylene glycol.

In the retro-aldol route, the carbohydrate is converted over a retro-aldol catalyst to intermediates, and the intermediates are then catalytically converted over a hydrogenation catalyst ("Hcat") to ethylene glycol and/or propylene glycol. The sought initially-occurring retro-aldol reaction is endothermic and requires a high temperature, e.g., often over 230° C., to provide a sufficient reaction rate to preferentially favor the conversion of carbohydrate to intermediates over the hydrogenation of carbohydrate to polyol such as sorbitol.

Catalysts used for the retro-aldol conversion are typically homogeneous and comprise tungsten and thus exit the reaction system with the product. Various proposals have been made to separate the monoethylene glycol and propylene glycol from the effluent of the reactor and recycle at least a portion of the remainder which contains tungsten to the reactor. See, for instance, U.S. Pat. Nos. 10,294,181 and 10,647,646 and U.S. Patent Application Publication 2021/0087128. While a recycle can conserve tungsten, tungsten species can form during use that are catalytically inactive or have reduced or undesirable catalytic activities.

Tungsten can also be recovered, e.g., by ion exchange or precipitation, and the recovered tungsten can be converted to catalytically active species for retro-aldol conversions. See, U.S. Patent Application Publication 2021/0087128.

Processes for making lower glycols from carbohydrates via the retro-aldol process are sought to recover tungsten compound from process, including purge, streams, which processes are easily operated, require little energy and provide recovered tungsten compound that has desirable catalytic activity for retro-aldol conversions.

SUMMARY

The processes of this invention involve an energy efficient and efficacious method for recovering tungsten from processes for making lower glycols from carbohydrates via the retro-aldol process. The processes involve the integration of ion-exclusion chromatography for the selective recovery of tungsten compounds, and if desired, recycle of tungsten compounds, while providing a higher boiling organic phase that can, if desired, be subjected to hydrogenolysis to enhance the conversion of carbohydrate to lower glycol.

By this invention integrated processes are provided for the catalytic conversion of carbohydrate to ethylene glycol and/or propylene glycol using a homogeneous, tungsten-containing retro-aldol catalyst. In these processes, the carbohydrate is subjected to retro-aldol conversion and hydrogenation to provide a reaction product containing ethylene glycol and/or propylene glycol, other reaction process including organic acids, itols and tungsten species. Ethylene glycol and propylene glycol are separated from the reaction product for purification, and at least a portion of the remaining fraction ("retained fraction") is subjected to ion exclusion chromatography to provide an eluant containing tungsten species and a subsequent eluant containing organic acids and a substantially reduced concentration of tungsten species. At least a portion of the eluant containing tungsten species can be recycled for reuse directly or with intervening unit operations to enhance the catalytic activity of the tungsten species.

It has been found that despite the tungsten species being a very small portion of the retained fraction, a significant portion of the tungsten, often at least about 60, and sometimes more than about 70 or 80, percent (based on atomic tungsten) can be recovered by ion exclusion chromatography with at least 90 percent by mass of the organics being separated into the subsequent eluant phase. Thus, the tungsten-containing eluant is suitable for recycle without undue build-up of non-reactive organics in the reaction zone, and any intervening treatments of the tungsten species in the eluant to be recycled involve the treatment of a reduce volume of liquid. And, with an intervening treatment such as pH adjustment, the reduced content of organic acids results in less pH adjustment agent being required for a desired pH change to convert the tungsten compounds to those desired for recycle.

In accordance with this invention, catalytic processes are provided for producing a lower glycol comprising at least one of ethylene glycol and propylene glycol from a carbohydrate-containing feed that comprises at least one of aldose- and ketose-yielding carbohydrate, which processes comprise:

(a) continuously or intermittently supplying the feed to a reaction zone having therein dissolved tungsten compounds at least one of which is homogeneous, tungsten-containing retro-aldol catalyst and at least one heterogeneous hydrogenation catalyst, said liquid medium being at catalytic conversion conditions including the presence of dissolved hydrogen, to produce a reaction product containing said lower glycol and one or more higher boiling point coproducts comprising sorbitol, erythritol, threitol and glycerin;

(b) continuously or intermittently withdrawing liquid medium that contains reaction product and dissolved tungsten compounds from the reaction zone;

(c) subjecting at least a portion of the withdrawn liquid medium to one or more unit operations to remove at least a portion of the lower glycol in a separated fraction and provide a retained liquid phase containing dissolved tungsten compounds and higher boiling point coproducts with a mass ratio of higher boiling coproducts to tungsten compounds calculated as the metal of greater than about 4:1; and (d) contacting at least a portion of the retained liquid phase with an ionic resin for ion exclusion chromatography, to provide a first eluted fraction containing dissolved tungsten compounds and a mass ratio of higher boiling coproducts to tungsten compounds calculated as the metal of less than about 5:1, preferably less than about 1:1, and contacting the ionic resin with sufficient solvent to provide at least one subsequent eluted fraction containing one or more higher boiling point coproducts and a lower concentration of tungsten (calculated as the metal) than that of the retained liquid phase, often less than about 10 parts by mass of tungsten compounds calculated as the metal per 100 parts by mass of higher boiling coproducts.

In preferred processes of this invention, at least about 90 mass percent of the tungsten compounds contained in the retained liquid phase contacted with the ion exchange resin are in the first eluted fraction. Preferably, at least a portion of the first eluted fraction is recycled to step (a), and in some instances, the first eluted fraction is provided at a pH of from about 6.5 to 8 before being passed to step (a). In some instances at least a portion of the tungsten compounds in the recycled, first eluted fraction is half neutralized tungstic acid. If desired, the subsequent eluted fraction is subjected to hydrogenolysis conditions to convert itols to lower glycol.

This invention also pertains to producer composition of matter comprising dissolved tungsten compound and one or more higher boiling point polyols comprising sorbitol, erythritol, threitol and glycerin wherein the mass ratio of total higher boiling polyol to tungsten compounds calculated as the metal is less than about 5:1, preferably less than about 1:1 and sometimes between about 0.01:1 and 1:1.

DETAILED DISCUSSION

All patents, published patent applications and articles referenced herein are hereby incorporated by reference in their entirety.

Definitions

As used herein, the following terms have the meanings set forth below unless otherwise stated or clear from the context of their use.

Where ranges are used herein, the end points only of the ranges are stated so as to avoid having to set out at length and describe each and every value included in the range. Any appropriate intermediate value and range between the recited endpoints can be selected. By way of example, if a range of between 0.1 and 1.0 is recited, all intermediate values (e.g., 0.2, 0.3. 0.63, 0.815 and so forth) are included as are all intermediate ranges (e.g., 0.2-0.5, 0.54-0.913, and so forth).

The use of the terms "a" and "an" is intended to include one or more of the element described.

Admixing or admixed means the formation of a physical combination of two or more elements which may have a uniform or non-uniform composition throughout and includes, but is not limited to, solid mixtures, solutions and suspensions.

Aldose means a monosaccharide that contains only a single aldehyde group (—CH═O) per molecule and having the generic chemical formula $C_n(H_2O)_n$. Non-limiting examples of aldoses include aldohexose (all six-carbon, aldehyde-containing sugars, including glucose, mannose, galactose, allose, altrose, idose, talose, and gulose); aldopentose (all five-carbon aldehyde containing sugars, including xylose, lyxose, ribose, and arabinose); aldotetrose (all four-carbon, aldehyde containing sugars, including erythrose and threose) and aldotriose (all three-carbon aldehyde containing sugars, including glyceraldehyde).

Aldose-yielding carbohydrate means an aldose or a di- or polysaccharide that can yield aldose upon hydrolysis. Sucrose, for example, is an aldose-yielding carbohydrate even though it also yields ketose upon hydrolysis.

Aqueous and aqueous medium or solution mean that water is present but does not require that water be the predominant component. For purposes of illustration and not in limitation, a solution of 90 volume percent of ethylene glycol and 10 volume percent water would be an aqueous solution. Aqueous solutions include liquid media containing dissolved or dispersed components such as, but not in limitation, colloidal suspensions and slurries.

Bio-sourced carbohydrate feedstock means a product that includes carbohydrates sourced, derived or synthesized from, in whole or in significant part, to biological products or renewable agricultural materials (including, but not limited to, plant, animal and marine materials) or forestry materials.

Calculated as the metal means calculation as elemental metal regardless of the molecular structure of the metal-containing compound.

Catalyst for converting the carbohydrate means one or more catalysts to effect the catalytic conversion which would both the retro-aldol catalyst and the hydrogenation catalyst ("Hcat"), each of which can comprise one or a mixture of catalysts. The catalyst can contain one or more catalytic metals, and for Hcats, include supports, binders and other adjuvants. Catalytic metals are metals that are in their elemental state or are ionic or covalently bonded. The term catalytic metals refers to metals that are not necessarily in a catalytically active state, but when not in a catalytically active state, have the potential to become catalytically active. Catalytic metals can provide catalytic activity or modify catalytic activity such as promotors, selectivity modifiers, and the like.

Commencing contact means that a fluid starts a contact with a component, e.g., a medium containing a homogeneous catalyst or heterogeneous catalyst, e.g., Hcat, but does not require that all molecules of that fluid contact the catalyst.

Compositions of aqueous solutions are determined using gas chromatography for lower boiling components, usually components having 3 or fewer carbons and a normal boiling point less than about 300° C., and high performance liquid chromatography for higher boiling components, usually 3 or more carbons, and those components that are thermally unstable.

Conversion efficiency of aldohexose to ethylene glycol is reported in mass percent and is calculated as the mass of ethylene glycol contained in the product solution divided by the mass of aldohexose theoretically provided by the carbohydrate feed and thus includes any aldohexose per se contained in the carbohydrate feed and the aldohexose theoretically generated upon hydrolysis of any di- or polysaccharide contained in the carbohydrate feed.

Hexitol means a six carbon compound having the empirical formula of $C_6H_{14}O_6$ with one hydroxyl per carbon.

High shear mixing involves providing a fluid traveling at a different velocity relative to an adjacent area which can be achieved through stationary or moving mechanical means to effect a shear to promote mixing. As used herein, the components being subjected to high shear mixing may be immiscible, partially immiscible or miscible.

Hydraulic distribution means the distribution of an aqueous solution in a vessel including contact with any catalyst contained therein.

Immediately prior to means no intervening unit operation requiring a residence time of more than one minute exists.

Intermittently means from time to time and may be at regular or irregular time intervals.

Ion exclusion chromatography involves an adsorbent material that is saturated with the same mobile ions (cationic or anionic) as are present in the feed, and because it is saturated, similar ions are repelled by the adsorbent material. Ion exclusion chromatography can use ion exchange resins beds acting as a charged solid separation medium. The ion exclusion chromatographic techniques using porous resin beds can serve to effect size exclusion separations such that molecules can be separated by size and molecular weight with larger and heavier molecules being eluted first.

Itol means a carbon compound containing at least two hydroxyl groups with one hydroxyl on each carbon atom.

Ketose means a monosaccharide containing one ketone group per molecule. Non-limiting examples of ketoses include ketohexose (all six-carbon, ketone-containing sugars, including fructose, psicose, sorbose, and tagatose), ketopentose (all five-carbon ketone containing sugars, including xylulose and ribulose), ketotetrose (all four-carbon, ketose containing sugars, including erythrulose), and ketotriose (all three-carbon ketose containing sugars, including dihydroxyacetone).

Ketose-yielding carbohydrate means a ketose or a di- or polysaccharide or hemicellulose that can yield ketose or ketose precursor upon hydrolysis. Most sugars are ring structures under ambient conditions and thus the ketose form occurs under the conditions of the process of this invention. Sucrose, for example, is a ketose-yielding carbohydrate even though it also yields aldose upon hydrolysis. For purposes herein, carbohydrates that produce both aldose and ketose will be deemed ketose-yielding carbohydrate except as the context requires otherwise.

Liquid medium means the liquid in the reactor. The liquid is a solvent for the carbohydrate, intermediates and products and for the homogeneous, tungsten-containing retro-aldol catalyst. Typically and preferably, the liquid contains at least some water and is thus termed an aqueous medium.

Lower glycol is ethylene glycol or propylene glycol or mixtures thereof.

The pH of an aqueous solution is determined at ambient pressure and temperature. In determining the pH of, for example the aqueous, hydrogenation medium or the product solution, the liquid is cooled and allowed to reside at ambient pressure and temperature for 2 hours before determination of the pH. Where the aqueous solution contains less than about 50 mass percent water, e.g., in a glycol-rich medium, water is added to a sample to provide a solution containing about 50 mass percent water. For purposes of consistency, the dilution of solutions is to the same mass percent water.

pH control agents means one or more of buffers and acids or bases.

A pressure sufficient to maintain at least partial hydration of a carbohydrate means that the pressure is sufficient to maintain sufficient water of hydration on the carbohydrate to retard caramelization. At temperatures above the boiling point of water, the pressure is sufficient to enable the water of hydration to be retained on the carbohydrate.

A rapid diffusional mixing is mixing where at least one of the two or more fluids to be mixed is finely divided to facilitate mass transfer to form a substantially uniform composition.

A reactor can be one or more vessels in series or in parallel and a vessel can contain one or more zones. A reactor can be of any suitable design for continuous operation including, but not limited to, tanks and pipe or tubular reactor and can have, if desired, fluid mixing capabilities. Types of reactors include, but are not limited to, laminar flow reactors, fixed bed reactors, slurry reactors, fluidized bed reactors, moving bed reactors, simulated moving bed reactors, trickle-bed reactors, bubble column and loop reactors.

Separation unit operations are one or more operations to selectively separate chemicals, including, but not limited to, chromatographic separation, sorption, membrane separation, flash separation, distillation, rectification, and evaporation.

Soluble means able to form a single liquid phase or to form a colloidal suspension.

Solubilized tungsten compounds are dissolved tungsten compounds or colloidally suspended tungsten compounds in the reaction medium.

Vapor/liquid separation is a separation providing one or more vapor streams and one or more liquid streams and can be based upon chromatographic separation, cyclic sorption, membrane separation, flash separation, distillation, rectification, and evaporation (e.g., thin film evaporators, falling film evaporators and wiped film evaporators).

Carbohydrate Feed

The processes of this invention use a carbohydrate feed that contains an aldohexose-yielding carbohydrate or ketose-yielding carbohydrate, the former providing under retro-aldol reaction conditions, an ethylene glycol-rich product and the latter providing a propylene glycol-rich product. Where product solutions containing a high mass ratio of ethylene glycol to propylene glycol are sought, the carbohydrate in the feed comprises at least about 90, preferably at least about 95 or 99, mass percent of aldohexose-yielding carbohydrate. Often the carbohydrate feed comprises a carbohydrate polymer such as starch, cellulose, or partially to essentially fully hydrolyzed fractions of such polymers or mixtures of the polymers or mixtures of the polymers with partially hydrolyzed fractions.

The carbohydrate feed is most often at least one of pentose and hexose or compounds that yield pentose or hexose. Examples of pentose and hexose include xylose, lyxose, ribose, arabinose, xylulose, ribulose, glucose, mannose, galactose, allose, altrose, idose, talose, and gulose fructose, psicose, sorbose, and tagatose. Most bio-sourced carbohydrate feedstocks yield glucose upon being hydrolyzed. Glucose precursors include, but are not limited to, maltose, trehalose, cellobiose, kojibiose, nigerose, nigerose, isomaltose, β,β-trehalose, α,β-trehalose, sophorose, laminaribiose, gentiobiose, and mannobiose. Carbohydrate polymers and oligomers such as hemicellulose, partially hydrolyzed forms of hemicellulose, disaccharides such as sucrose, lactulose, lactose, turanose, maltulose, palatinose, gentiobiulose, melibiose, and melibiulose, or combinations thereof may be used.

If desired, the carbohydrate feed can be treated to remove one or more impurities, especially impurities that have the potential to affect one or more of the catalysts. For instance, moities that can oxidize or sulfide one or more of the catalysts used in the processes.

The carbohydrate feed can be solid or, preferably, in a liquid suspension or dissolved in a solvent such as water. Where the carbohydrate feed is in a non-aqueous environment, it is preferred that the carbohydrate is at least partially hydrated. Non-aqueous solvents include alkanols, diols and polyols, ethers, or other suitable carbon compounds of 1 to 6 carbon atoms. Solvents include mixed solvents, especially mixed solvents containing water and one of the aforementioned non-aqueous solvents. Certain mixed solvents can have higher concentrations of dissolved hydrogen under the conditions of the hydrogenation reaction and thus reduce the potential for hydrogen starvation. Preferred non-aqueous solvents are those that can be hydrogen donors such as isopropanol. Often these hydrogen donor solvents have the hydroxyl group converted to a carbonyl when donating a hydrogen atom, which carbonyl can be reduced under the conditions in the reaction zone. Most preferably, the carbohydrate feed is provided in an aqueous solution. In any event, the volume of feed and the volume of raw product withdrawn need to balance to provide for a continuous process.

Further considerations in providing the carbohydrate to the reaction zone are minimizing energy and capital costs. For instance, in steady state operation, the solvent contained in the feed exits the reaction zone with the raw products and needs to be separated in order to recover the sought glycol products.

Preferably, the feed is introduced into the reaction zone in a manner such that undue concentrations of feed that can result in hydrogen starvation are avoided. With the use of a greater number of multiple locations for the supply of carbohydrate per unit volume of the reaction zone, the more concentrated the carbohydrate in the feed can be. In general, the mass ratio of water to carbohydrate in the carbohydrate feed is preferably in the range of 4:1 to 1:4. Aqueous solutions of 600 or more grams per liter of certain carbohydrates such as dextrose and sucrose are sometimes commercially available.

In some instances, recycled hydrogenation solution having a substantial absence of hydrogenation catalyst, or aliquot or separated portion thereof, is added as a component to the carbohydrate feed. The recycled hydrogenation solution can be one or more of a portion of the raw product stream or an internal recycle where hydrogenation catalyst is removed. Suitable solid separation techniques include, but are not limited to, filtration and density separation such as cyclones, vane separators, and centrifugation. With this recycle, the amount of fresh solvent for the feed is reduced, yet the carbohydrate is fed at a rate sufficient to maintain a high conversion per unit volume of reaction zone. The use of a recycle, especially where the recycle is an aliquot portion of the raw product stream, enables the supply of low concentrations of carbohydrate to the reaction zone while maintaining a high conversion of carbohydrate to ethylene glycol. Additionally, it is feasible to maintain the recycle stream at or near the temperature in the reaction zone and it as it contains tungsten-containing catalyst, retro-aldol conversion can occur prior to entry of the feed into the reaction zone. With the use of recycled hydrogenation solution, the mass ratio of carbohydrate to total recycled product stream and added solvent is often in the range of about 0.05:1 to 0.4:1, and sometimes between about 0.1:1 to 0.3:1. The recycled raw product stream is often between about 20 and 80 volume percent of the product stream.

The carbohydrate contained in the carbohydrate feed is provided at a rate of at least 50 or 100, and preferably, between about 150 to 500 grams per liter of reactor volume per hour. Optionally, a separate reaction zone can be used that contains retro-aldol catalyst with an essential absence of hydrogenation catalyst.

The Conversion Process

In the processes, the carbohydrate feed is introduced into solvent that contains catalyst for the catalytic conversion and hydrogen. The solvent is frequently water but can be lower alcohol or polyalcohols of 1 to 6 carbons, especially methanol, ethanol, n-propanol and isopropanol.

The carbohydrate feed may or may not have been subjected to retro-aldol conditions prior to being introduced into the reaction zone, and the carbohydrate feed may or may not have been heated through the temperature zone of 170° C. to 230° C. upon contacting the liquid medium in the reaction zone. Thus, in some instances the retro-aldol reactions may not occur until the carbohydrate feed is introduced into the liquid medium, and in other instances, the retro-aldol reactions may have at least partially occurred prior to the introduction of the carbohydrate feed into the liquid medium in the reaction zone. It is generally preferred to quickly disperse the carbohydrate feed in the liquid medium especially where the hydrogenation medium is used to provide direct heat exchange to the carbohydrate feed. This dispersion can be achieved by any suitable procedure including, but not limited to, the use of mechanical and stationary mixers and rapid diffusional mixing. The use of multiple ports to introduce the feed into the reactor also facilitates quick dispersion.

The preferred temperatures for retro-aldol reactions are typically between about 230° C. and 300° ° C., and more preferably between about 240° C. and 280° C., although retro-aldol reactions can occur at lower temperatures, e.g., as low as 90° C. or 150° C. The pressures (absolute) are typically in the range of about 15 to 200 bar (1500 to 20,000 kPa), say, between about 25 and 150 bar (2500 and 15000 kPa). Retro-aldol reaction conditions include the presence of retro-aldol catalyst. A retro-aldol catalyst is a catalyst that catalyzes the retro-aldol reaction. Examples of tungsten compounds that can provide retro-aldol catalyst include, but are not limited to, heterogeneous and homogeneous catalysts, including catalyst supported on a carrier, comprise tungsten and its oxides, sulfates, phosphides, nitrides, carbides, halides, acids and the like. Tungsten carbide, soluble phosphotungstens, tungsten oxides supported on zirconia, alumina and alumina-silica are also included. Preferred catalysts are provided by soluble tungsten compounds and mixtures of tungsten compounds. Soluble tungstates include, but are not limited to, ammonium and alkali metal, e.g., sodium and potassium, paratungstate, partially neutralized tungstic acid, ammonium and alkali metal metatungstate and ammonium and alkali metal tungstate. Often the presence of ammonium cation results in the generation of amine by-products that are undesirable in the lower glycol product. Without wishing to be limited to theory, the species that exhibit the catalytic activity may or may not be the same as the soluble tungsten compounds introduced as a catalyst. Rather, a catalytically active species may be formed as a result of exposure to the retro-aldol reaction conditions. Tungsten-containing complexes are typically pH dependent. For instance, a solution containing sodium tungstate at a pH greater than 7 will generate sodium metatungstate when the pH is lowered. The form of the complexed tungstate anions is generally pH dependent. The rate that complexed anions formed from the condensation of tungstate anions are formed is influenced by the concentration of tungsten-containing anions. A preferred retro-aldol catalyst comprises ammonium or alkali metal tungstate that becomes partially neutralized with acid, preferably an organic acid of 1 to 6 carbons such as, but without limitation, formic acid, acetic acid, glycolic acid, and lactic acid. The partial neutralization is often between about 25 and 75%, i.e., on average between 25 and 75% of the cations of the tungstate become acid sites. The partial neutralization may occur prior to introducing the tungsten-containing compound into the reactor or with acid contained in the reactor.

The concentration of retro-aldol catalyst used may vary widely and will depend upon the activity of the catalyst and the other conditions of the retro-aldol reaction such as acidity, temperature and concentrations of carbohydrate. Typically, the retro-aldol catalyst is provided in an amount to provide between about 0.01 or 0.05 and 100, say, between about 0.02 or 0.1 and 50, grams of tungsten calculated as the elemental metal per liter of aqueous, hydrogenation medium. The retro-aldol catalyst can be added as a mixture with all or a portion of the carbohydrate feed or as a separate feed to the liquid medium or with recycling liquid medium or any combination thereof. Where the retro-aldol catalyst comprises two or more tungsten species and they may be fed to the reaction zone separately or together. In some preferred aspects, the carbohydrate feed is admixed with retro-aldol catalyst prior to contacting hydrogenation catalyst. The admixture is preferably at a pH of greater than 4, and often greater than 5.5, and in some instances between about 6 and 7.5, say 6.5 to 6.8.

Frequently the carbohydrate feed is subjected to retro-aldol conditions prior to being introduced into the hydrogenation medium in the reaction zone containing hydrogenation catalyst. Preferably the introduction into the aqueous, hydrogenation medium occurs in less than one minute, and most often less than 10 seconds, from the commencement of subjecting the carbohydrate feed to the retro-aldol conditions. Some, or all of the retro-aldol reaction can occur in the reaction zone containing the hydrogenation catalyst. In any event, the most preferred processes are those having a short duration of time between the retro-aldol conversion and hydrogenation.

Under many process conditions useful in the processes of this invention, tungsten-containing precipitates can form and may be suspended or deposited on surfaces, including the surface of the hydrogenation catalyst where the activity of the hydrogenation catalyst can be affected.

The hydrogenation, that is, the addition of hydrogen atoms to an organic compound without cleaving carbon-to-carbon bonds, can be conducted at a temperature in the range of about 100° C. or 120° ° C. to 300° C. or more. Typically, the hydrogenation medium is maintained at a temperature of at least about 230° C. until substantially all carbohydrate is reacted to have the carbohydrate carbon-carbon bonds broken by the retro-aldol reaction, thereby enhancing selectivity to ethylene and propylene glycol. Thereafter, if desired, the temperature of the hydrogenation medium can be reduced. However, the hydrogenation proceeds rapidly at these higher temperatures. Thus, the temperatures for hydrogenation reactions are frequently between about 230° C. and 300° C., say, between about 240° C. and 280° C. Typically, in the retro-aldol process the pressures (absolute) are typically in the range of about 15 to 200 bar (1500 to 20,000 kPa), say, between about 25 and 150 bar (2500 and 15000 kPa). The hydrogenation reactions require the presence of hydrogen as well as hydrogenation catalyst. Hydrogen has low solubility in aqueous solutions. The concentration of hydrogen in the aqueous, hydrogenation medium is increased with increased partial pressure of hydrogen in the reaction zone. The pH of the aqueous, hydrogenation medium is often at least about 2.5 or 3, say, between about 3 or 3.5 and 8, and in some instances between about 3.5 or 4 and 7.5.

The hydrogenation is conducted in the presence of a hydrogenation catalyst. Frequently the hydrogenation catalyst is a supported, heterogeneous catalyst. It can be deployed in any suitable manner, including, but not limited to, fixed bed, fluidized bed, trickle bed, moving bed, slurry bed, loop bed, such as Buss Loop® reactors available from BUSS ChemTech AG, and structured bed. One type of reactor that can provide high hydrogen concentrations and rapid heating is cavitation reactor such as disclosed in U.S. Pat. No. 8,981,135 B2, herein incorporated by reference in its entirely. Cavitation reactors generate heat in localized regions and thus the temperature in these localized regions rather the bulk temperature of the liquid medium in the reaction zone is the temperature process parameter for purposes of this invention. Cavitation reactors are of interest for this process since the retro-aldol conversion can be very rapid at the temperatures that can be achieved in the cavitation reactor.

Nickel, ruthenium, palladium and platinum are among the more widely used reducing metal catalysts. However, many reducing catalysts will work in this application. The catalysts may be supported or unsupported such as Raney nickel. The reducing catalyst can be chosen from a wide variety of supported transition metal catalysts. One particularly favored catalyst for the reducing catalyst in this process is a supported, Ni—Re catalyst. A similar version of Ni/Re or Ni/Ir can be used with good selectivity for the conversion of the formed glycolaldehyde to ethylene glycol. Nickel-rhenium is a preferred reducing metal catalyst and may be supported on alumina, alumina-silica, silica or other supports. Supported Ni—Re catalysts with B as a promoter are useful. Generally, for slurry reactors, a supported hydrogenation catalyst is provided in an amount of less than 10, and sometimes less than about 5, say, about 0.1 or 0.5 to 3, grams per liter of nickel (calculated as elemental nickel) per liter of liquid medium in the reactor. As stated above, not all the nickel in the catalyst is in the zero-valence state, nor is all the nickel in the zero-valence state readily accessible by glycol aldehyde or hydrogen. Hence, for a particular hydrogenation catalyst, the optimal mass of nickel per liter of liquid medium will vary. For instance, Raney nickel catalysts would provide a much greater concentration of nickel per liter of liquid medium. Frequently in a slurry reactor, the hydrogenation catalyst is provided in an amount of at least about 5 or 10, and more often, between about 10 and 70 or 100, grams per liter of aqueous, hydrogenation medium and in a packed bed reactor the hydrogenation catalyst comprises about 20 to 80 volume percent of the reactor. In some instances, the weight hourly space velocity is between about 0.01 or 0.05 and 1 $hr^{-1}$ based upon total carbohydrate in the feed. Preferably the residence time is sufficient that glycol aldehyde and glucose are less than 0.1 mass percent of the reaction product, and most preferably are less than 0.001 mass percent of the reaction product.

The carbohydrate feed is at least 50 grams of carbohydrate per liter per hour, and is often in the range of about 100 to 700 or 1000, grams of carbohydrate per liter per hour.

In the processes of this invention, the combination of reaction conditions (e.g., temperature, hydrogen partial pressure, concentration of catalysts, hydraulic distribution, and residence time) are sufficient to convert at least about 95, often at least about 98 or 99, mass percent and sometimes essentially all of the carbohydrate that yields aldose or ketose. It is well within the skill of the artisan having the benefit of the disclosure herein to determine the set or sets of conditions that will provide the sought conversion of the carbohydrate.

Ion Exclusion Chromatographic Separation

Ion exclusion chromatographic separation is used in the processes of this invention to obtain as the sought product, a producer composition rich in dissolved tungsten compound, and reject lower glycol and higher boiling coproducts which are recovered in a subsequent eluant. The producer composition has a substantially reduced ratio of lower glycol and higher boiling coproducts to the tungsten compounds as compared to that ratio in the retained liquid phase. Accordingly, recovery of the tungsten compounds can be undertaken without significant loss of lower glycol and higher boiling coproducts, and the subsequent eluant can be purged and/or treated without the undue loss of tungsten compounds.

The feed to the ionic resin for the ion exclusion chromatographic separation is at least a portion, which may be an aliquot or aliquant portion, of the retained liquid phase from the separation of lower glycol from the reaction product. Any suitable unit operation or operations can be used to separate lower glycol including, but not limited to, chromatographic separation, sorption, membrane separation, flash separation, distillation, rectification, and evaporation. Vapor liquid separations are typically used. In some instances, the withdrawn reaction product is depressurized with the gases being captured for recovery of the hydrogen and removal of unwanted gaseous by-products such as methane and carbon dioxide. A vapor/liquid separation then provides a vaporous overhead containing at least a portion of the lower glycol and other volatilized compounds such as acetic acid. The retained liquid phase often contains lower glycol in addition to the higher boiling point coproducts and tungsten compounds. Where a distillation, flash or evaporation is used, the bottoms temperature is frequently in the range of about 120° C. to 200° C., and the vapor phase is at a pressure of between about 500 to 10,000, say, 1000 to 5000, kPa absolute. As most of the water and total ethylene glycol and propylene glycol are passed to the vapor phase in these embodiments of this invention, the liquid phase may sometimes be rich in heavies and thus increase the difficulties in processing. Accordingly, water is preferably added to the liquid phase from the vapor/liquid separator to provide a liquid comprising at least about 25, and sometimes at least about 35, mass percent water.

The composition of the retained liquid phase will depend upon, among other things, the unit operations used to separate lower glycol and the extent that these unit operations are used to remove lower glycol; the conversion process operation and reaction product composition; the concentration of tungsten compounds in the reaction products and whether water or other solvent is added to the retained liquid phase, and if so, how much. In most instances, lower glycol will be the most prevalent organic species in the retained liquid phase, and the retained liquid phase will also contain higher boiling coproducts, i.e, sorbitol, erythritol, threitol, and glycerin, and potentially carboxylic acids or esters. The retained liquid phase will also contain tungsten compounds. The tungsten compounds include soluble tungsten compounds and may include solid tungsten compounds such as tungsten bronzes and tungstic acid. The tungsten compounds are typically oxygenated tungsten anions such as tungstic acid, partially neutralized tungstic acid, tungstate, metatungstate, paratungstate, and the like, and may or may not have catalytic activity. One or more unit operations can occur to the retained liquid phase that can change its composition such as the addition of water or other solvent, or further vapor/liquid separation or sorption or chemical reaction.

The processes of this invention may be used with retained liquid phases that vary widely in the concentration of lower glycol as both ethylene glycol and propylene glycol elute from the ion exclusion chromatography after most of the tungsten compound have been eluted. Accordingly, lower glycol may comprise as much as about 50 or 60, say, between about 10 and 50, mass percent of the organics in the retained liquid phase. As little of the higher boiling coproducts are separated with lower glycol from the reaction product, a ratio of the mass of higher boiling coproducts to tungsten compounds (calculated as the metal) is useful to describe the chromatographic separation. In most instances this ratio is greater than about 4:1, and can be up to about 300:1 or 500:1, and in some instances between about 25:1 to 100:1.

All, or an aliquot or aliquant portion of, the retained liquid phase can be contacted with the ionic resin for the ion exclusion chromatographic separation. The contact may be continuous, semi-continuous, intermittent or batch. The retained liquid phase may be diluted, e.g., with water to decrease viscosity. Sometimes the viscosity at the temperature of contact with the ionic resin is less than about 100 Pascal seconds, and in some instances between about 0.1 and 50 Pascal seconds. The temperature of the retained liquid phase contacting the ionic resin is below that which adversely affects the resin, and is often in the range of about 0° C. to 150° C., say, between about 10° C. and 100° C. The pressure of the feed can fall within a wide range, e.g., from about 100 to 100,000 kPa absolute. The liquid hourly space velocity of the feed to the ionic resin will depend, upon other things, the nature of the feed and its composition, the sought degree of chromatographic separation; the nature of the ionic resin; and the design of the equipment used for the ion exclusion chromatography. Frequently, the liquid hourly space velocity is in the range of about 0.1 to 50 $hr^{-1}$.

The contact with the ionic resin can be in a moving or fixed bed, and can be in a batch, semi-continuous or continuous mode of operation. The ionic resin is typically packed in a column, and the feed is passed through the column to provide an eluate. Solvent is then passed through the column to elute other components in the feed. The determination of the diameter and height of the columns is well within the skill of the ordinary artisan in the field of ion exclusion chromatographic separations having the benefit of the disclosure herein. In some instances, the processes of this invention use a simulated moving bed (SMB). An SMB apparatus can, if desired, operate continuously. An SMB apparatus comprises multiple columns containing ionic resin connected in series. The valve and column arrangement is such that the points of addition of feed and solvent and the points of withdrawal of the desired product rich in tungsten compound (the producer composition) and the organic product, in the series of columns, are periodically moved from column to column. The movement is counter to the flow of liquid in the series of columns so as to give the impression of a moving bed. For a general discussion of SMB, see, for instance, U.S. Pat. Nos. 2,985,589; 4,340,724; and 6,479,716.

Any suitable, ionic resin can be used including strong and weak anionic resins and strong and weak cationic resins. The resins can be gel or, preferably, macroreticular resins. In some instances, the resins have a degree of crosslinking of at least about 3, say, up to about 15 or more, percent. Frequently resins having a degree of cross linking of at least about 6, preferably at least about 8, percent are used to enhance stability and to provide more porosity. In some instances, the porosity is such that the organics are eluted without using undue amounts of solvents. In these instances, the focus of the chromatographic separation is on achieving the sought tungsten compound containing eluant, and there is no desire to use the chromatographic separation for separation of the various organics. The effectiveness of an ionic resin for separation of the tungsten-containing fraction from the organics can be perceived by comparing the total excluded volume with the total included volume. In general, the greater the differences, the more effective the separation. Total excluded volume is the amount of solvent required to exclude an aliquot of an ionic compound on the resin such as tungstate. The total included volume is the amount of solvent required to elute an aliquot of a non-ionic compound such as glycerin.

Many commercially-available ionic resins comprise one of polystyrene, polymethacrylate and polyacrylate, and often are cross linked using an agent such as divinyl benzene. The ionic functionality can be provided, in the case of anionic resins, amines and in the case of cationic resins, carboxylic, phosphonic or sulfonic groups. In some instances, the size of the ionic resin particles is in the range of 100 to 10,000 or more microns in major dimension. The preferred ionic resins are macroreticular cationic resins having carboxylic or sulfonic functionality due to the stability of the resins. Preferably, the cation associated with the fresh cationic resin is not one that forms precipitates with the tungsten compound, although, after multiple cycles, any cation that forms precipitate would be eluted. Sodium cationic resins are preferred. In some instance the cationic resin is a polystyrene sulfonate strong cation exchange resin with a degree of cross-linking of at least about 4, say, at least about 6, e.g., between about 6 and 15, percent.

Drawings

Figure 1:
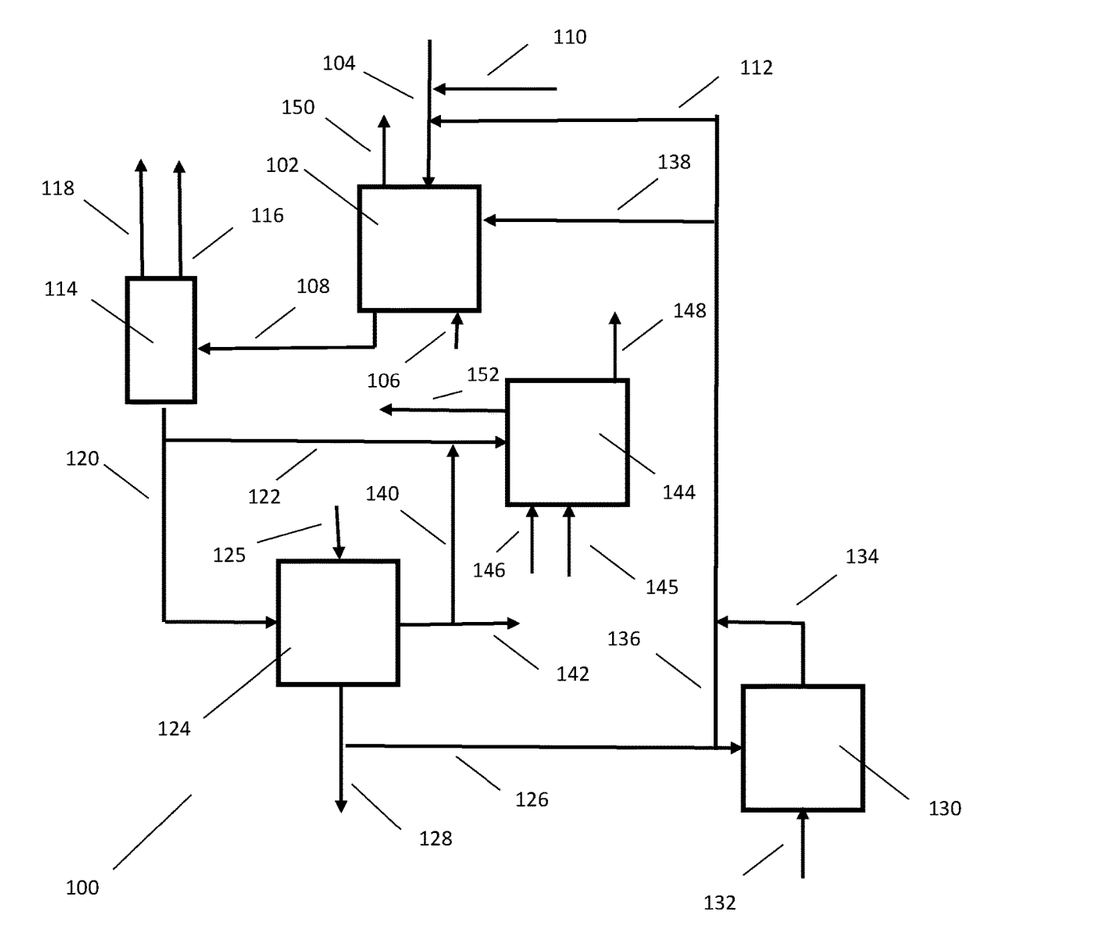
FIG. 1 is a schematic diagram of an apparatus for practicing the processes of this invention.

Reference is made to the drawing which is provided to facilitate the understanding invention but is not intended to be in limitation of the invention. The drawing omits minor equipment such as pumps, compressors, valves, instruments, heat exchangers and other devices the placement of which and operation thereof are well known to those practiced in chemical engineering. The drawing also omits ancillary unit operations.

With reference to FIG. 1, apparatus 100 comprises catalytic conversion reactor 102 for the conversion of carbohydrate to ethylene glycol and/or propylene glycol. The reactor may be a single vessel or two or more vessels of the same or different design in parallel or in series. At least one vessel contains heterogeneous hydrogenation catalyst. At least one vessel contains retro-aldol catalyst, especially soluble retro-aldol catalyst.

As shown, carbohydrate feed is passed via line 104 to reactor 102, and hydrogen for the catalytic conversion is passed to reactor 102 via line 106. Tungsten compound for the retro aldol catalyst is provided at least by lines 110 and 112 as will be discussed later. A reaction product is withdrawn from reactor 102 via line 108.

The reaction product contains one or both of ethylene glycol and propylene glycol, and it contains higher boiling coproducts (sorbitol, erythritol, threitol, glycerol, and 1,2-butanediol). Since the catalytic conversion is conducted at elevated pressure in the presence of hydrogen, the reaction product contains dissolved hydrogen and dissolved tungsten compound.

As depicted, the reaction product is passed to vapor/liquid separator 114. The vapor/liquid separator may comprise one or more unit operations, e.g., with recovery of hydrogen and light gases followed by one or more unit operations to recover water and ethylene glycol and propylene glycol from the reaction product. Hydrogen and other light gases such as carbon dioxide and methane, are withdrawn via line 116 for recovery of hydrogen for recycle. The liquid components can then be subjected to one or more unit operations to recover lower glycol including additional vapor/liquid separations or liquid/liquid separations such as selective membrane permeation and selective sorption. In another mode, the vapor/liquid separation provides a vaporous overhead that contains a substantial portion of the ethylene glycol and propylene glycol in the reaction product. Often, at least about 30, and more frequently at least about 50, say, about 50 to 75 or 95, mass percent of the total ethylene glycol and propylene glycol are provided to the overhead. The overhead in line 118 would be passed to unit operations for the refining of ethylene glycol and propylene glycol as well as separation of normally gaseous components not removed with the hydrogen and light gases.

All or a portion (aliquot or aliquant) of the retained liquid phase is withdrawn from vapor/liquid separator 114 via line 120. Shown is an embodiment where higher boiling components in the retained liquid is subjected to catalytic conditions to convert at least a portion of the higher boiling coproducts to lower glycol, e.g., by hydrogenolysis. A portion of the retained liquid phase can be drawn off of line 120 by line 122 for such catalytic processing even though it contains tungsten compound. In this manner, the volume of retained liquid phase being subjected to ion exclusion chromatography can be controlled, especially as plant production is varied. As discussed later, the organic phase from ion exclusion chromatography can also be subjected to such catalytic processing.

All or the remaining portion of the retained liquid phase in line 120 is passed to a simulated moving bed unit 124 for ionic exclusion chromatography to provide a separated tungsten compound-containing eluted phase and a separated organic-containing eluted phase. If desired, the portion of the retained liquid phase may be subjected to chemical and/or physical unit operations to reduce the presence of solids, e.g., filtration, oxidation, or the like.

For purposes of discussion and not in limitation of the invention, the simulated moving bed contains ten columns of strong cationic resin in series with valving to add and withdraw liquid from each column. A volume of retained liquid phase is introduced over a predetermined time into one of the series of columns, and liquid that passes through that column is passed to the next column in the series and so on for all ten columns. After the predetermined time, the feed of retained liquid phase is passed to the previous column in the series. This sequencing is repeated continuously. A tungsten-containing eluted phase is withdrawn from a column later in the direction of the flow of the liquid, say, from the fourth column from the column in which the retained liquid phase is introduced. The selection of the column is well within the skill of the art of ion exclusion chromatography in simulated moving beds and will depend, in part, upon the portion of the tungsten compound to be recovered and the concentration of organics that can be tolerated in the tungsten compound-containing eluted phase. The ion exclusion chromatography can be operated such that higher percentages of the tungsten compound going to the tungsten compound-containing eluted phase, e.g., at least about 90, and preferably at least about 95 or 99, atomic percent of the tungsten. Alternatively, the ion exclusion chromatography can be operated such that the tungsten-containing eluted phase Contamination with organic compound is usually not as critical, however, especially where the tungsten compound-containing eluted phase is subjected to pH adjustment, e.g., to convert tungsten complexes to partially neutralized tungstate, minimization of organic acids is preferred to reduce the amount of base required for the pH adjustment. Frequently, the mass ratio of total organics to tungsten compound (calculated as the element) is less than about 10:1, and in some instances less than about 1:1, say, about 0.1:1. The tungsten compound-containing eluted phase is withdrawn from the simulated moving bed 124 via line 126. If desired, a portion of the eluted phase can be withdrawn from line 126 via line 128 for purge or recovery of tungsten.

The relative volume of the purge stream will depend upon, among other things, the portion of the tungsten species that are rendered catalytically inactive or relatively inactive during the reaction processes such as tungstic acid or tungsten bronzes. The purge can be continuous or intermittent. In instances where a purge is used, often between about 5 and 40, say, between about 10 and 25, mass percent of the eluted phase is purged. Tungsten can be recovered from the purge stream. Any suitable process or combination of processes can be used to recover the tungsten including, but not limited to, ion exchange and acidification to precipitate tungstic acid for separation.

All or a portion of the tungsten compound-containing eluted phase can be passed continuously or intermittently via line 126 to treatment vessel 130. As the tungsten compound containing eluted phase may contain a number of tungsten compounds, including, but not limited to, meta- and para-tungstates, tungstic acid, and partially neutralized tungstate, conversion of the species to partially neutralized tungstate facilitates providing more predictable retro-aldol catalytic activity for the recycled tungsten compound. As shown, base such as sodium hydroxide, is added to treatment vessel 130 via line 132 in an amount sufficient to adjust the pH to between about 6 and 8, and frequently between about 6.5 and 6.8. The treated effluent is withdrawn from vessel 130 via line 134 for recycle to reactor 102.

Returning to line 126, if desired, all or a portion of the tungsten compound-containing eluted phase can be directed continuously or intermittently to line 136 for recycle to reactor 102 and bypassing treatment vessel 130. Where bypassing does occur, typically between about 20 to 100, and sometimes between about 25 and 80, mass percent of the tungsten compound-containing eluted phase is passed from line 126 to line 136. In some instances, the bypass tungsten compound-containing eluted phase is such that the pH of the mixture of feed, organic recycle and retro-aldol catalyst in line 104 is at least about 4.5, preferably at least about 5, say, 5.5 to 8, and sometimes between about 5.5 and 6.8.

The treated effluent in line 134 from treatment vessel 130 is depicted as being combined with any bypass in line 136 for recycle to reactor 102. All or a portion of the recycled tungsten compound in line 136 can be directed via line 112 to line 104 for admixing with feed, of all or a portion of the recycled tungsten compound in line 136 can be passed via line 138 directly into reactor 102. In instances where the recycled tungsten compound is added directly to reactor 102, it is especially beneficial if it has passed through treatment vessel 130 and has a pH in the higher range, e.g., between about 6.5 and 8, such that it can be used in part to control pH in the reactor.

Returning to simulated moving bed 124, a solvent, such as water, is added via line 125 at the fifth column to elute organics from the sorption media in simulated moving bed 124 to provide an eluant containing organics at the last column in the series. By the simulated moving bed sequencing, the organic eluant is withdrawn via line 140. A portion of this eluant is typically purged via line 142 to assure steady state operating compositions in reactor 102. The purge is often in the range of 1 to 30 mass percent of the eluant, the greater percentages frequently being used when a significant portion of the retained liquid phase is bypassed via line 122. All or a portion of the organic eluant and bypassing retained liquid phase can be passed directly to reactor 102, or as shown, subjected to a unit operation to enhance the conversion efficiency of the feed to monoethylene glycol. In the drawing, the organic eluant in line 140 is combined with any retained liquid phase in line 122 and passed to hydrogenolysis reactor. In hydrogenolysis reactor 144, hydrogen supplied via line 150 and hydrogenolysis catalyst are contacted with the organics supplied by line 122 under hydrogenolysis conditions to provide a hydrogenolysis product containing, among other things, monoethylene glycol and propylene glycol and a reduced concentration of carboxylic acids and higher boiling point coproducts. It should be understood that the hydrogen for the hydrogenolysis can be off gases withdrawn from reactor 102 via line 150. Hydrogenolysis conditions often include a temperature of between about 150° C. or 200° ° C. and 240° ° C., preferably between about 200° ° C. and 230° C.; a hydrogen partial pressure of between about 2500 to 12,000, say, about 5000 to 10,000, kPa, and a liquid hourly space velocity of between about 0.01 to 20 $hr^{-1}$. Any suitable hydrogenolysis catalyst can be used such as those containing one or more of nickel, cobalt, ruthenium, rhodium, platinum, and palladium. For the sake of convenience, the hydrogenolysis catalyst can be the Hcat used for the hydrogenation.

Hydrogenolysis product is withdrawn from hydrogenolysis reactor 144 via line 146 and gases are withdrawn via line 148 for recovery and purification. All or a portion of the hydrogenolysis product in line 146 can be passed to line 108 for recovery of ethylene glycol and propylene glycol in vapor/liquid separator 114.

It is claimed:

1. A producer composition of matter comprising dissolved tungsten compound and one or more higher boiling point polyols comprising sorbitol, erythritol, threitol and glycerin wherein the mass ratio of total higher boiling polyol to tungsten compounds calculated as the metal is less than about 5:1.

2. The producer composition of claim 1 wherein the mass ratio of total higher boiling polyol to tungsten compounds calculated as the metal is between about 0.01:1 and 1:1.

* * * * *